(12) United States Patent
Stalcup et al.

(10) Patent No.: US 10,350,332 B2
(45) Date of Patent: Jul. 16, 2019

(54) FIXATION OF ORTHOPAEDIC DEVICES

(71) Applicant: SMed-TA/TD, LLC, Columbia City, IN (US)

(72) Inventors: Gregory C. Stalcup, Fort Wayne, IN (US); Troy D. Knapp, Alachua, FL (US); Joseph W. Jurick, Fort Wayne, IN (US); Paul S. Nebosky, Fort Wayne, IN (US); Kreigh R. Williams, Fort Wayne, IN (US)

(73) Assignee: SMed-TA/TD, LLC, Columbia City, IN (US)

( * ) Notice: Subject to any disclaimer, the term of this patent is extended or adjusted under 35 U.S.C. 154(b) by 0 days.

(21) Appl. No.: 15/602,778

(22) Filed: May 23, 2017

(65) Prior Publication Data

US 2017/0252492 A1 Sep. 7, 2017

Related U.S. Application Data

(62) Division of application No. 14/204,129, filed on Mar. 11, 2014.

(Continued)

(51) Int. Cl.
*A61B 17/80* (2006.01)
*A61L 31/14* (2006.01)
(Continued)

(52) U.S. Cl.
CPC ........ *A61L 31/146* (2013.01); *A61B 17/7098* (2013.01); *A61B 17/8028* (2013.01);
(Continued)

(58) Field of Classification Search
None
See application file for complete search history.

(56) References Cited

U.S. PATENT DOCUMENTS 6,193,721 B1 * 2/2001 Michelson ......... A61B 17/1604
606/246
8,475,505 B2 7/2013 Nebosky et al.
(Continued)

OTHER PUBLICATIONS

Notification of Transmittal of the International Search Report and the Written Opinion of the International Searching Authority, or the Declaration dated Aug. 21, 2014 for International Patent Application No. PCT/US2014/024498 (15 pages).

(Continued)

*Primary Examiner* — Sameh R Boles
(74) *Attorney, Agent, or Firm* — Taylor IP, P.C.

(57) ABSTRACT

The present invention provides an orthopedic implant including a base device having a device surface and a fixation material attached to at least one portion of the device surface. The fixation material is configured to provide a minimally sufficient adhesive force to resist natural pull out caused by forces acting on the base device after implantation and bone growth. Also provided is a method of manufacturing an orthopedic implant. A base device with a device surface is provided and a minimally sufficient adhesive force, that can resist natural pull out caused by forces acting on the base device after implantation and bone growth, is determined. A proper amount of fixation material sufficient to provide an adhesive force equal to the minimally sufficient adhesive force is determined and fixation material is applied to the device. When the proper amount of fixation material is applied to the device surface, application is stopped.

14 Claims, 8 Drawing Sheets

Related U.S. Application Data

(60) Provisional application No. 61/787,507, filed on Mar. 15, 2013.

(51) Int. Cl.
*A61L 31/16* (2006.01)
*A61L 31/02* (2006.01)
*A61L 31/06* (2006.01)
*A61B 17/70* (2006.01)
*A61B 17/84* (2006.01)
*A61B 17/86* (2006.01)

(52) U.S. Cl.
CPC ........ *A61B 17/846* (2013.01); *A61B 17/8625* (2013.01); *A61L 31/022* (2013.01); *A61L 31/06* (2013.01); *A61L 31/16* (2013.01); *A61B 2017/8655* (2013.01); *A61L 2300/404* (2013.01); *A61L 2300/41* (2013.01); *A61L 2300/414* (2013.01); *A61L 2400/18* (2013.01)

(56) References Cited

U.S. PATENT DOCUMENTS

| | | |
|---|---|---|
| 2004/0267263 A1 | 12/2004 | May |
| 2010/0003640 A1 | 1/2010 | Damstra et al. |
| 2010/0042213 A1 | 2/2010 | Nebosky et al. |
| 2010/0042214 A1 | 2/2010 | Nebosky et al. |
| 2011/0029081 A1 | 2/2011 | Malone |
| 2011/0123951 A1 | 5/2011 | Lomicka |
| 2012/0029432 A1 | 2/2012 | Sweeney |

OTHER PUBLICATIONS

International Preliminary Report on Patentability and Written Opinion dated Sep. 15, 2015 for International Application No. PCT/US2014/024498 (10 pages).

Extended European Search Report dated Oct. 13, 2016 for European Application No. 14 76 8586 (8 pages).

* cited by examiner

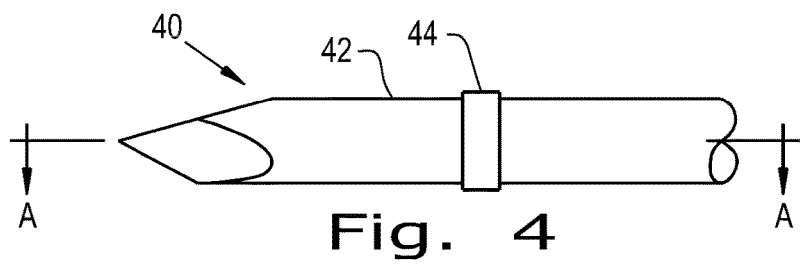
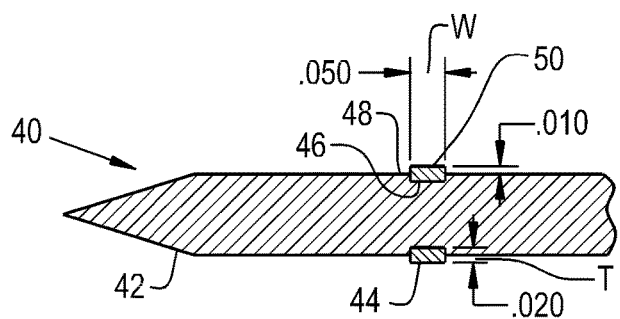
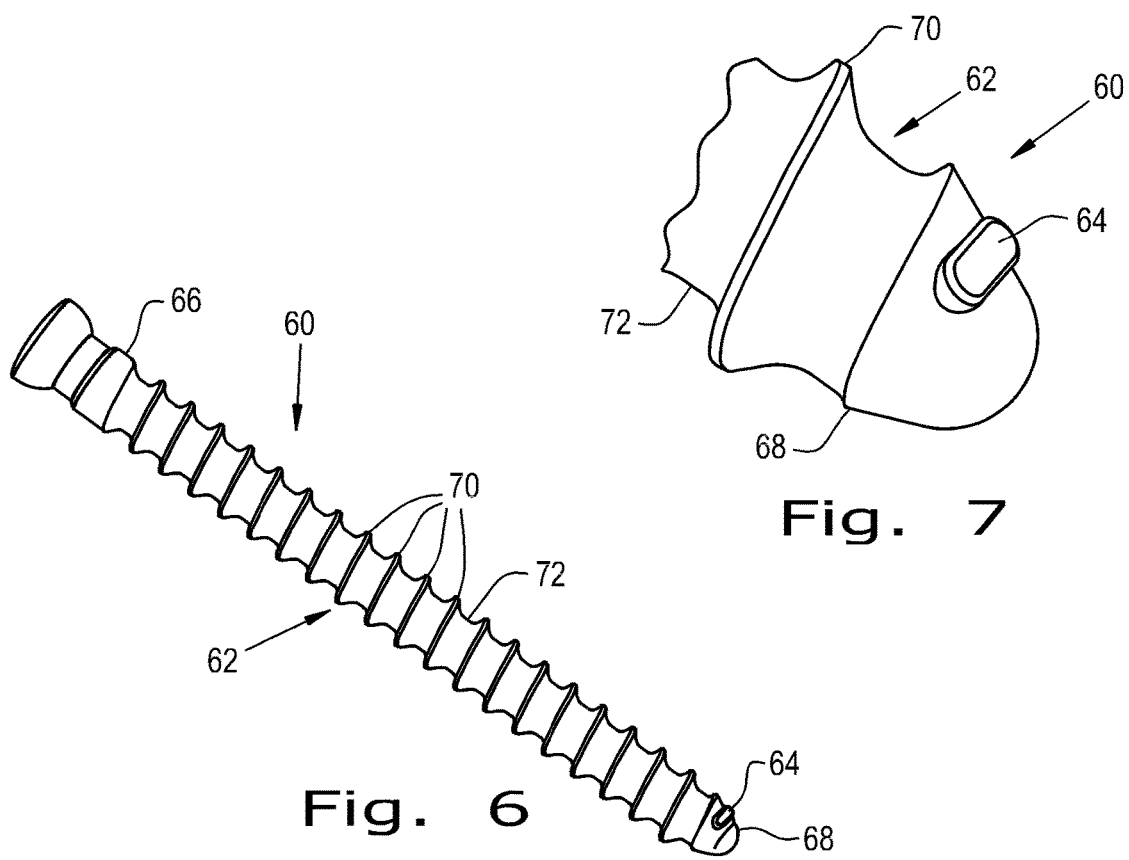

FIXATION OF ORTHOPAEDIC DEVICES

CROSS REFERENCE TO RELATED APPLICATIONS

This is a division of U.S. patent application Ser. No. 14/204,129, entitled "FIXATION OF ORTHOPAEDIC DEVICES," filed Mar. 11, 2014, which is incorporated herein by reference. U.S. patent application Ser. No. 14/204,129 is a non-provisional application based upon U.S. provisional patent application Ser. No. 61/787,507, entitled "FIXATION OF ORTHOPAEDIC DEVICES", filed Mar. 15, 2013, which is incorporated herein by reference.

BACKGROUND OF THE INVENTION

1. Field of the Invention

The present invention relates to orthopaedic devices, and more particularly, to orthopaedic implants.

2. Description of the Related Art

Orthopaedic implants are known that are implanted into the body to achieve various surgical objectives. Such implants include bone pins, bone screws and bone plates. The implantation period of the implant can vary from a short period, such as a couple of days, to the end of a patient's life. During the implantation period, the implant will experience natural forces caused by surrounding anatomy structures due to static and dynamic conditions of the anatomy structures. These natural forces can cause the implant to either loosen from the implantation site or, worse, ultimately detach from the implant site.

To prevent the loosening and detachment of an orthopaedic implant from its implantation site, the implant is usually fixated to the implantation site by bone screws, which must be screwed into the implantation site. The implant can also be bonded to the implantation site with an adhesive, such as bone cement, or materials can be attached to the implant that encourage natural ingrowth of tissue onto or into the implant. Natural tissue ingrowth will help to fixate the implant in place and can form a strong bond with the implant.

One problem that arises with implanted devices is that there is a risk that a revision surgery, to remove the implant, may be required due to reasons such as an incorrect placement, an unforeseen event or an infection causing the implant to prematurely fail. In such cases, removing the implant can be a traumatic event for anatomy structures around the site if a lot of force is required to loosen the implant and remove it.

A similar problem can occur with devices that are meant to be temporary, i.e., have a relatively short implantation period. The device can become too integrated with the body and become very difficult to remove, which can lead to trauma at the implantation site during removal.

What is needed in the art is an orthopaedic implant that can resist natural pull out but does not require excessive force to remove.

SUMMARY OF THE INVENTION

The present invention provides an orthopaedic implant with a fixation material attached to the implant that is configured to provide a minimally sufficient adhesive force to resist natural pull out of the implant caused by forces acting on the implant during implantation and bone ingrowth.

The invention in one form is directed to an orthopaedic implant including a base device with a device surface and a fixation material attached to the base device. The fixation material is attached to at least one portion of the device surface and is configured to provide a minimally sufficient adhesive force to resist natural pull out caused by forces acting on the base device after implantation and bone ingrowth The invention in another form is directed to a method of manufacturing an orthopaedic implant. The method includes providing a base device that has a surface area and determining a minimally sufficient adhesive force to resist natural pull out caused by forces acting on the base device after implantation and bone ingrowth. A proper amount of a fixation material sufficient to provide an adhesive force equal to the determined minimally sufficient adhesive force is determined and the fixation material is applied to the device surface. When the proper amount of the fixation material is applied to the device surface, application of the fixation material is stopped.

The invention in yet another form is directed to a method of performing an orthopaedic surgery. The method includes providing an orthopaedic implant having a device surface and a fixation material attached to the device surface. The fixation material is configured to provide a minimally sufficient adhesive force to resist natural pull out caused by forces acting on the base device after implantation and bone ingrowth. The orthopaedic implant is implanted at an implantation site within a patient. The implantation of the orthopaedic implant is revised by applying a revisionary force to the orthopaedic implant that is slightly greater than the minimally sufficient adhesive force.

An advantage of the present invention is that it provides an orthopaedic implant that can withstand natural pull out forces when implanted within a patient while not requiring excessive force to remove, if necessary.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 4 is a perspective view of another embodiment of an orthopaedic implant of the present invention;

FIG. 5 is a cross-sectional view of the orthopaedic implant shown in FIG. 4 along line A-A;

FIG. 6 is a perspective view of yet another embodiment of an orthopaedic implant of the present invention;

FIG. 7 is a sectional view of the orthopaedic implant shown in FIG. 6;

Corresponding reference characters indicate corresponding parts throughout the several views. The exemplifications set out herein illustrate embodiments of the invention and such exemplification are not to be construed as limiting the scope of the invention in any manner.

DETAILED DESCRIPTION OF THE INVENTION

Figure 1:
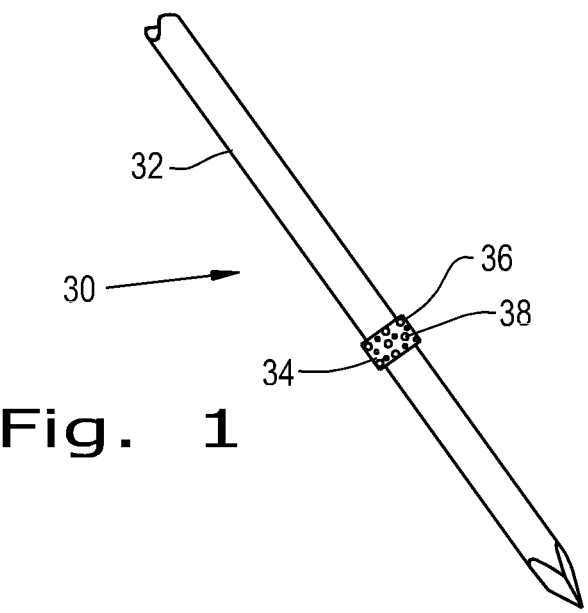
FIG. 1 is a perspective view of an embodiment of an orthopaedic implant of the present invention.

Referring now to the drawings, and more particularly to FIG. 1, there is shown an orthopaedic implant 30 which generally includes a base device 32 and a fixation material 34 attached to the base device 32. The base device 32 shown is a bone pin that can reside within a patient for a short period of time. The base device 32 can be constructed of metals commonly used in orthopaedic implants such as titanium, cobalt chrome and stainless steel. Alternatively, the base device can be constructed of biocompatible polymers such as polyether ether ketone (PEEK), polylactic acid (PLA), polyglycolic acid (PGA), polyethylene (PE) and blends thereof.

The fixation material 34 attached to the base device 32 is shaped as a thin band wrapped around the circumference of the base device 32. The fixation material 34 can be a porous polymer or metal that has a roughened surface 36 to provide immediate fixation of the device 30 due to frictional forces and to encourage quick tissue ingrowth into the fixation material 34. The roughened surface 36 can have customized surface properties for a specific tissue type and desired tissue ingrowth amount or rate. Such surface properties can include a surface energy density, wettability and electrostatic charge. Polymers and metals that can act as the fixation material 34 include PEEK, PLA, PGA, PE, titanium, cobalt chrome and stainless steel. Pores 38 of the fixation material 34 can be sized to allow or prevent ingrowth of tissue into the fixation material 34. Additionally, biologically active substances can be included in the pores 38 to encourage or limit tissue ingrowth into the fixation material 34, as well as provide other useful properties such as antimicrobial activity to reduce the risk of infection.

Figure 2:
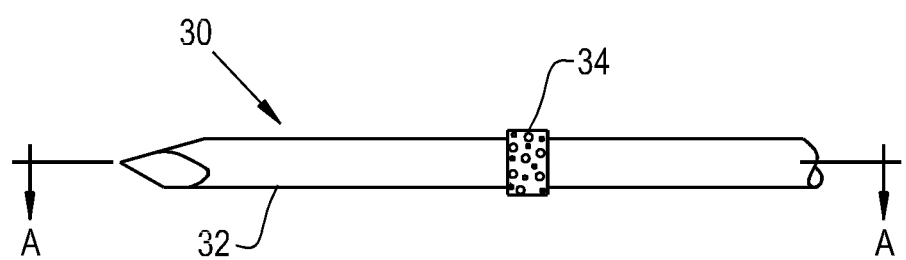
FIG. 2 is another perspective view of the orthopaedic implant shown in FIG. 1.
Figure 3:
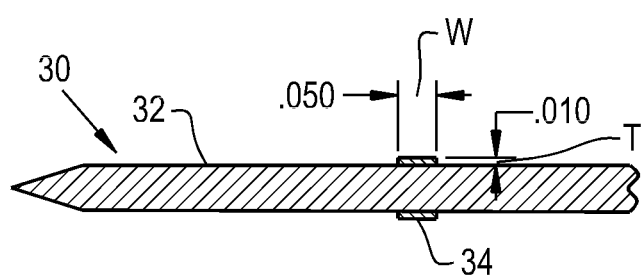
FIG. 3 is a cross-sectional view of the orthopaedic implant shown in FIG. 2 along line A-A.

As the orthopaedic implant 30 is a small diameter bone pin that will likely be removed within a few weeks of implantation, a strong interface between surrounding tissue and the orthopaedic implant 30 is undesirable as it will cause removal of the orthopaedic implant 30 to be unnecessarily difficult. As can be seen in FIGS. 2 and 3, only a relatively small band of fixation material 34 is necessary to provide a minimally sufficient adhesive force that will resist pull out of the orthopaedic implant 30 while it is implanted in a patient while not causing excessive adhesive force that could make the device 30 difficult to remove. As shown in FIG. 3, the fixation material 34 has a relatively low thickness T (0.010") and a width W ("0.050") significantly greater than the thickness T. For the orthopaedic device 30 shown, a thickness T range of about 0.005" to 0.015" and a width W range of about 0.020" to 0.125" can be appropriate dimensions for the fixation material 34 shaped as a band to provide the minimally sufficient adhesive force. It is also contemplated that there can be multiple fixation materials attached to the base device 32, which would alter the dimensions of each fixation material region. An additional design consideration when shaping and placing the fixation material 34 on a small diameter pin is that the pin won't provide much leverage to apply torque and overcome the adhesive force provided by the fixation material 34.

Referring now to FIGS. 4 and 5, an orthopaedic implant 40 is shown which includes a base device 42, shown here as a large diameter pin, with a fixation material 44 attached to the pin 42. The fixation material 44 can be the same as the fixation material 34 described previously. When utilizing a large diameter pin 42, the amount and geometry of the fixation material 44 will need to be changed to provide a minimally sufficient adhesive force that will resist natural pull out of the pin 42, due to increased size of the pin 42. As shown in FIGS. 4 and 5, the fixation material 44 can be shaped as a band around the circumference of the pin 42, similar to the previously described small diameter pin 32. The band of fixation material 44 can have a thickness T ranging from about 0.015" to 0.050" and a width W ranging from about 0.020" to 0.125". As can be seen in FIG. 5, the pin 42 can also have a groove 46 formed on the outer surface 48 of the pin 42 where the fixation material 44 attaches to the pin 42. The groove 46 can have a varying depth that changes how proud an outer surface 50 of the fixation material 44 is relative to the outer surface 48 of the pin 42. As seen in FIG. 5, the fixation material 44 has a thickness T of 0.020", but the outer surface 50 only elevates 0.010" relative to the outer surface 48 of the pin 42. Having the groove 46 in the pin 42 allows for a thicker fixation material 44, which will increase the potential bone ingrowth and adhesive force, with a smaller increase in the overall diameter of the device 40. The groove 46 also provides more surface area of the pin 42 to utilize for attachment to the fixation material 44. As opposed to a small diameter pin, a large diameter pin can have a larger minimally sufficient adhesive force but still be easily removed because the large diameter pin 42 provides more leverage to apply torque and overcome the adhesive force provided by the fixation material 44.

Referring now to FIGS. 6 and 7, an orthopaedic implant 60 is shown which includes a base device 62, shown as a bone screw, and a fixation material 64 attached to the bone screw 62. The bone screw 62 can be constructed of biocompatible metals and polymers, similar to previously described base devices, and the fixation material 64 can be made of a material similar to that of previously described fixation materials. The bone screw 62 has a head end 66, a distal end 68 and a plurality of threads 70 formed on a surface 72 of the bone screw 62. The fixation material 64 forms a small patch on the distal end 68 of the bone screw 62. The threads 70 of the bone screw 62 will provide some adhesive force to keep the bone screw 62 in place during implantation, so the fixation material patch 64 acts to provide additional adhesive force at the distal end 68, if necessary, to resist natural pull out of the bone screw 62.

Figure 8:
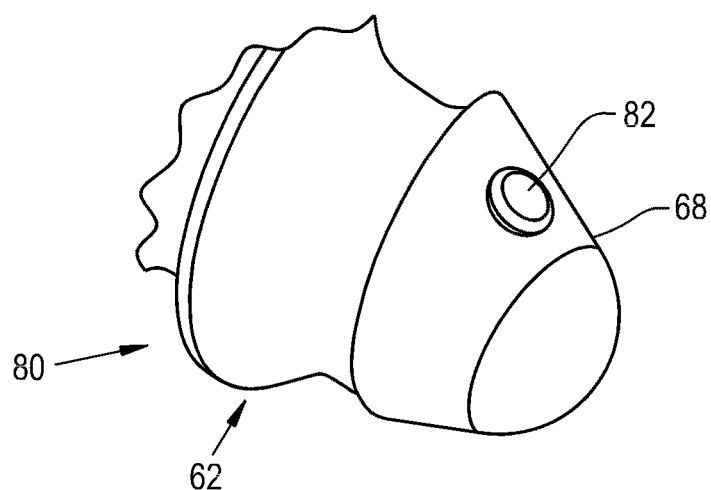
FIG. 8 is a sectional view of yet another embodiment of an orthopaedic implant of the present invention.

Referring now to FIG. 8, an orthopaedic implant 80 is shown which includes a bone screw 62 similar to that shown in FIGS. 6 and 7 having a fixation material 82 attached to the distal end 68 of the bone screw 62. The fixation material 82 can be formed from any fixation material previously described. In this embodiment, the fixation material 82 is formed as a "dot" of material on the distal end 68 of the bone screw 62 to provide additional adhesive force to the bone screw 62.

Figure 9:
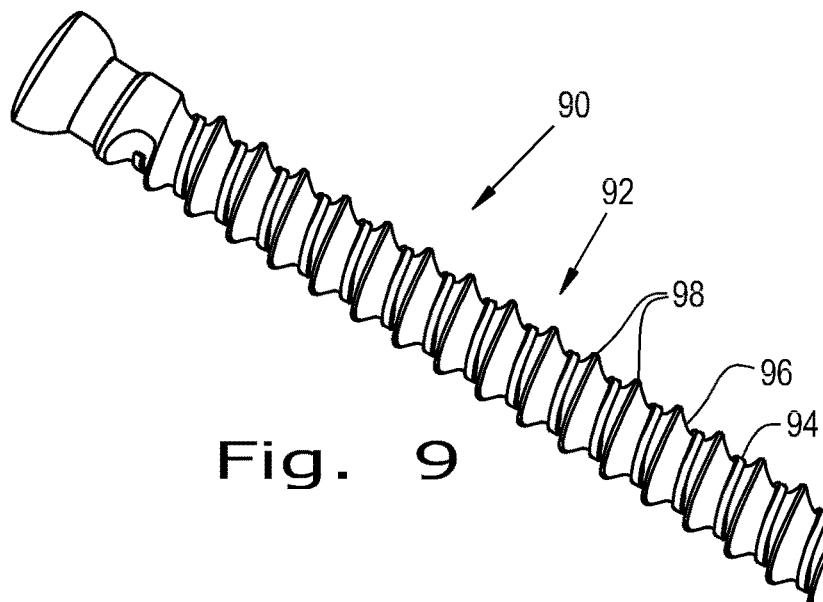
FIG. 9 is a perspective view of yet another embodiment of an orthopaedic implant of the present invention.
Figure 10:
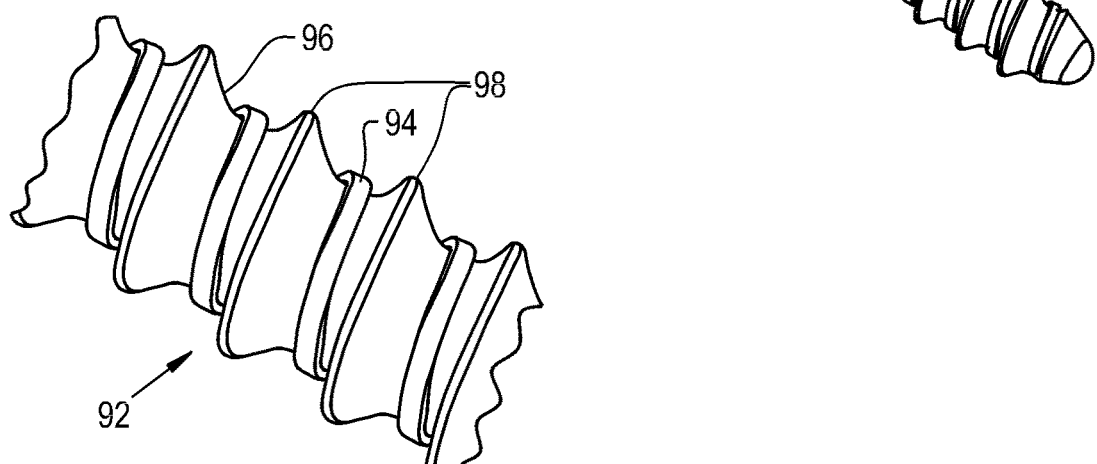
FIG. 10 is a sectional view of the orthopaedic implant shown in FIG. 9.

Referring now to FIGS. 9 and 10, an orthopaedic implant 90 is shown which includes a bone screw 92 similar to that shown in FIGS. 6, 7 and 8 having a fixation material 94 attached to a surface 96 of the bone screw 92 between threads 98 formed on the surface 96 of the bone screw 92. The fixation material 94 can be formed from any fixation material previously described. As can be seen, the fixation material 94 has a helical shape that wraps around the circumference of the bone screw 92 between the threads 98. In this configuration, the fixation material 94 provides a substantial amount of adhesive force to resist natural pull out of the device 90. Such a configuration may be desirable for bone screws that are intended to have a longer implantation period, where additional fixation of the bone screw is desirable.

Figure 11:
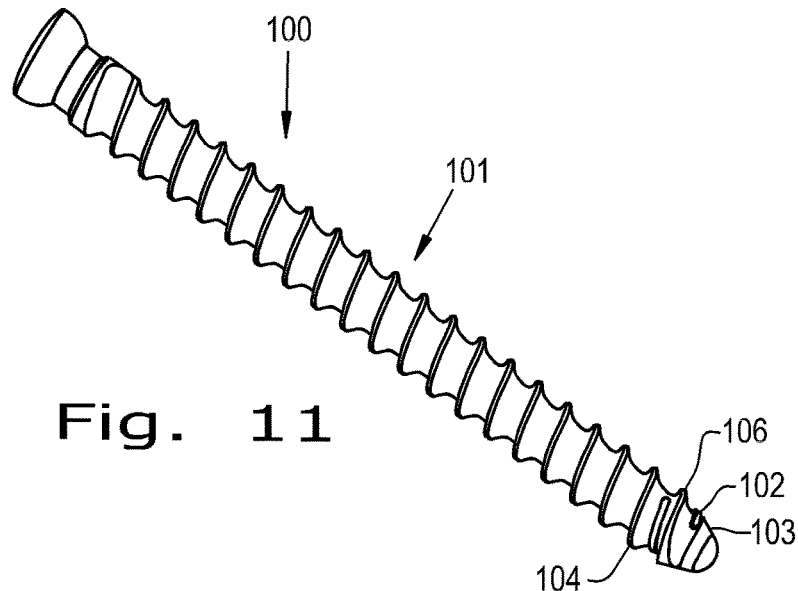
FIG. 11 is a perspective view of yet another embodiment of an orthopaedic implant of the present invention.
Figure 12:
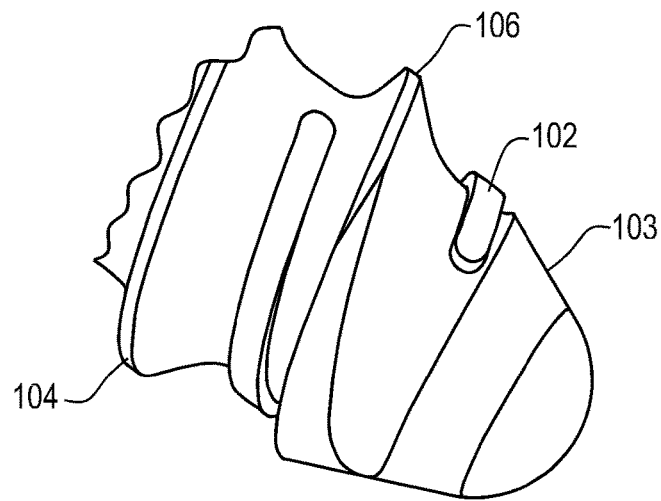
FIG. 12 is a sectional view of the orthopaedic implant shown in FIG. 11.

Referring now to FIGS. 11 and 12, an orthopaedic implant 100 is shown which includes a bone screw 101 similar to that shown in FIGS. 6, 7, 8 and 9 having a fixation material 102 attached near a distal end 103 of the bone screw 101 between the distal end 103 and threads 104 and 106. The fixation material 102 can be formed from any fixation material previously described. This configuration allows for the fixation material 102 to provide less fixation force than orthopaedic implant 90, previously described. Such a configuration is better suited for bone screws that are intended to have shorter implantation periods, where too much additional fixation of the bone screw would make removal unnecessarily difficult.

Figure 13:
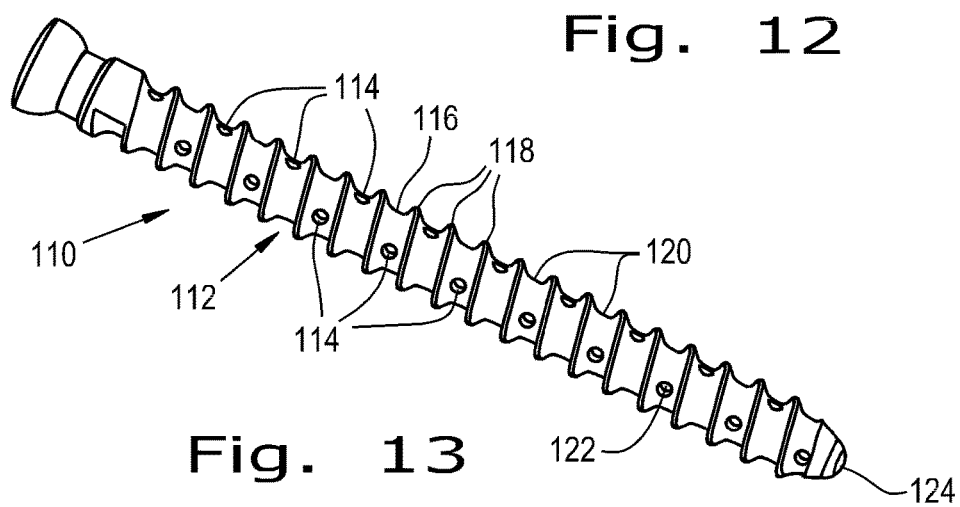
FIG. 13 is a perspective view of yet another embodiment of an orthopaedic implant of the present invention.
Figure 14:
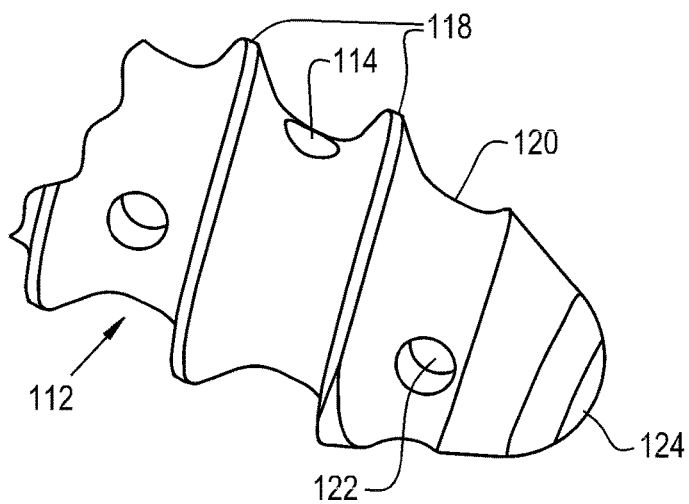
FIG. 14 is a sectional view of the orthopaedic implant shown in FIG. 13.
Figure 15:
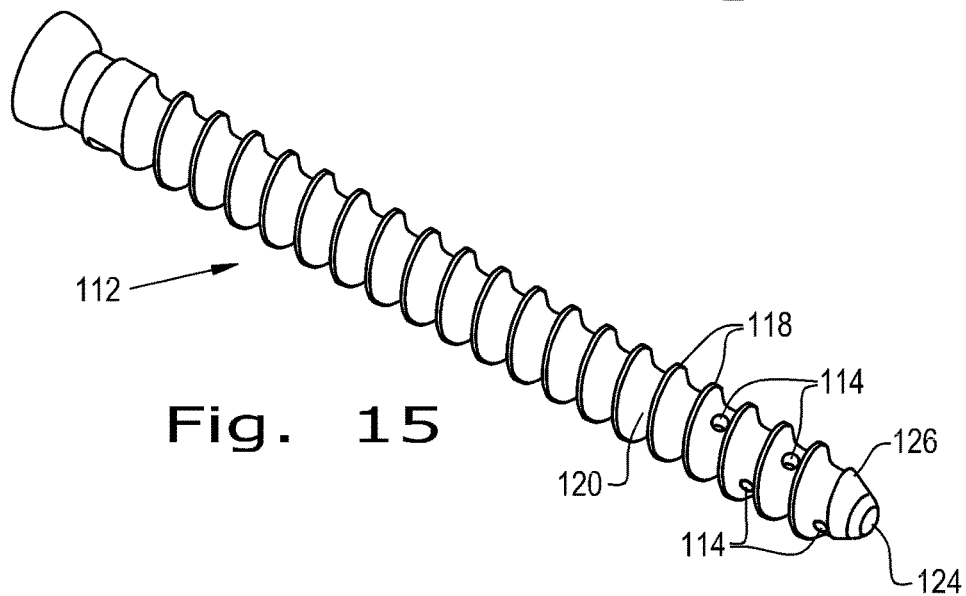
FIG. 15 is a perspective view of yet another embodiment of an orthopaedic implant of the present invention.
Figure 16:
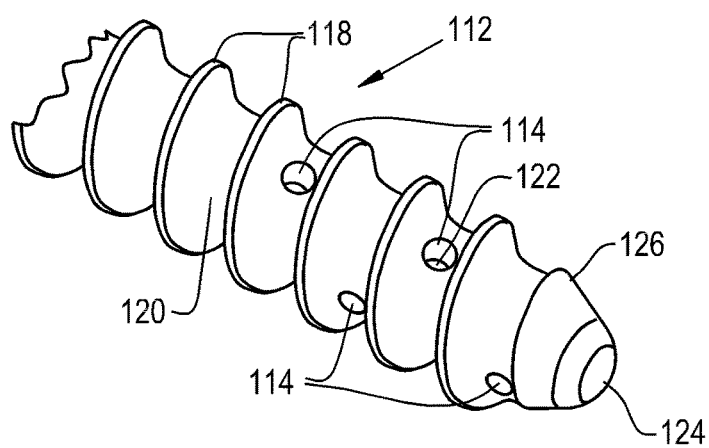
FIG. 16 is a sectional view of the orthopaedic implant shown in FIG. 15.

Referring now to FIGS. 13 and 14, an orthopaedic implant 110 is shown which includes a base device 112, shown as a bone screw, with holes 114 formed through a surface 116 of the bone screw 112 between threads 118. The holes 114 are located axially in valleys 120 between the threads 118 and go through to the centerline of the screw 112. The holes 114 can be placed along the full length of the screw 112. The screw 112 is a cannulated screw having an inner chamber 120 that has a fixation material 122 bonded inside the inner chamber 120. By having holes 114 and the fixation material 122 inside the inner chamber 120, tissue will be chemoattracted to the fixation material 122 and fill in the holes 114, forming a strong interface with the orthopaedic implant 110. A wall thickness (not shown) between the minor diameter of the bone screw 112 and the inner wall of the inner chamber 120 should be in a range of approximately 1 mm to 1.5 mm. Studies have shown that bone will bridge a gap of approximately 1 mm to 1.5 mm to grow into a porous material, such as the fixation material 122. FIGS. 15 and 16 show a similar embodiment, with fewer holes 114 formed through the bone screw 112 and the holes 114 being concentrated near a distal end 126 of the bone screw 112.

Figure 17:
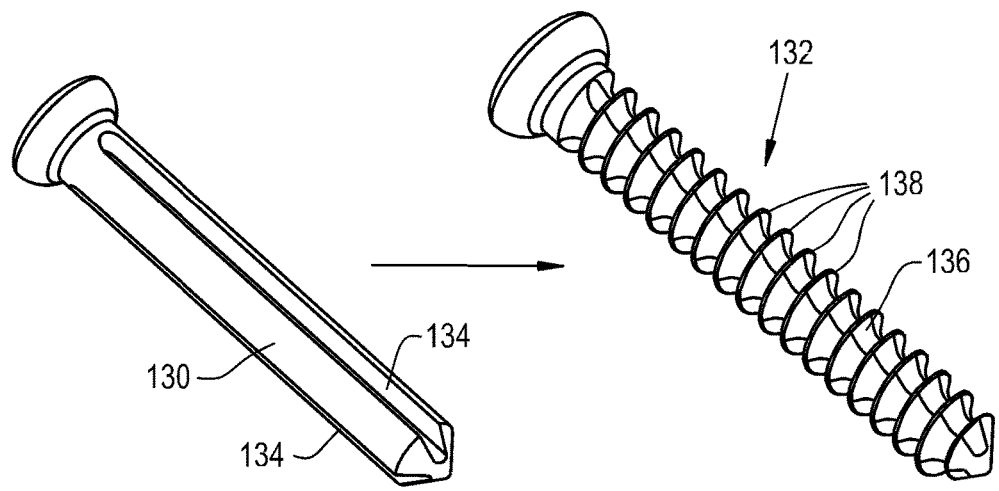
FIG. 17 is a before and after exploded view of forming yet another embodiment of an orthopaedic implant of the present invention.

Referring now to FIG. 17, a base device 130 is shown before and after being prepared into an orthopaedic implant 132 of the present invention. As can be seen, the base device 130 is a screw blank that has had elongated pockets 134 machined within. These elongated pockets 134 are filled with a fixation material 136, which can be any fixation material previously described. Following filling of the elongated pockets 134 with the fixation material 136, threads 138 can be cut into the base device 130 and fixation material 136 to form the completed orthopaedic implant 132. In this configuration, the threads 138 will be composed of approximately half fixation material 136 and half material of the base device 130, giving the orthopaedic implant 132 a substantial amount of fixation material 136 to provide adhesive force during implantation and also placing the fixation material 136 into intimate contact with surrounding anatomy structures during implantation. Such a configuration can be particularly useful when the orthopaedic implant 132 is intended to be a long-term implant.

Figure 18:
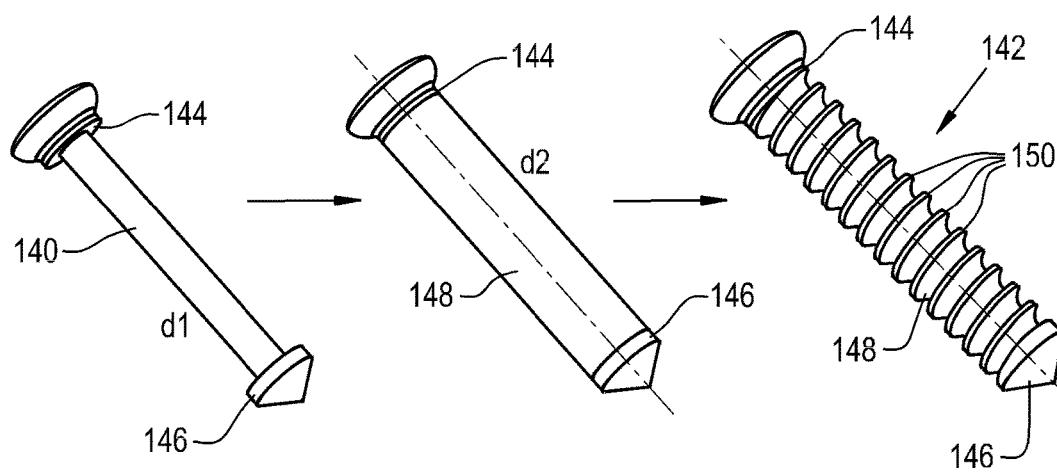
FIG. 18 is another before and after exploded view of forming yet another embodiment of an orthopaedic implant of the present invention.

Referring now to FIG. 18, a base device 140 is shown before and after being prepared into an orthopaedic implant 142. The base device 140 is a screw blank with a minor diameter d1 between a head end 144 and a distal end 146. A fixation material 148, which can be any fixation material previously described, is bonded to a section of the base device 140 having minor diameter d1 to create a diameter d2 similar to that of the head end 146 and distal end 148. Threads 150 are then formed into the fixation material 148 to create the completed orthopaedic implant 142.

Figure 19:
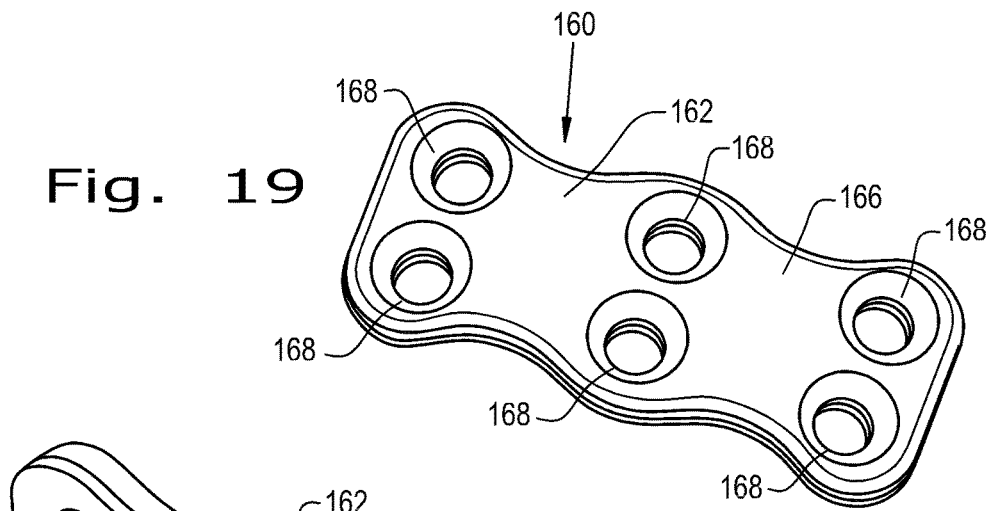
FIG. 19 is a perspective view of yet another embodiment of an orthopaedic implant of the present invention.
Figure 20:
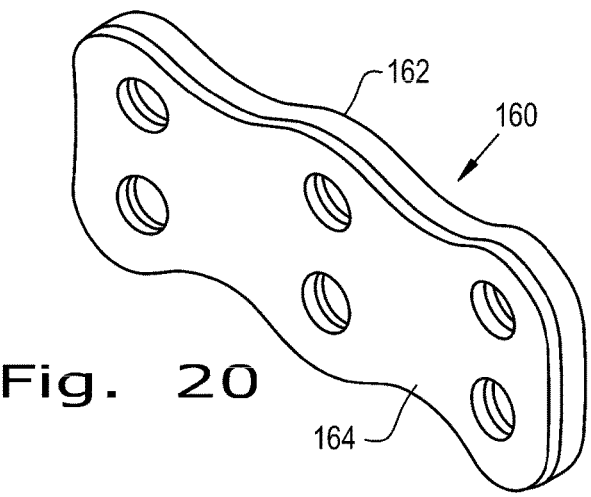
FIG. 20 is another perspective view of the orthopaedic implant shown in FIG. 19.

Referring now to FIGS. 19 and 20, an orthopaedic implant 160 is shown that includes a base device 162, shown as a bone plate, and a fixation material 164 attached to the bone plate 162. The bone plate 162 has a bare surface 166 and multiple openings 168 that are sized to allow bone screws (not shown) to be passed through. The openings 168 are shaped so that when the bone screws are driven into a bone, they will hold the bone plate 162 in place. The bone plate 162 can be made of biocompatible metals such as titanium, cobalt chrome and stainless steel, but can also be made of a biocompatible polymer such as PEEK. A polymer bone plate 162 could offer advantages over more common metal bone plates, such as higher compression and adjustable stiffening. The fixation material 164 is attached to a bottom surface (not shown) that is opposed to the bare surface 166 and will be in contact with the bone during implantation. The fixation material 164 can be any fixation material previously described. In this embodiment, the fixation material 164 forms a layer on the bottom surface of the bone plate 162. Since bone screws will be going through the openings 168, the fixation material 164 does not cover the openings 168. If the bone plate 162 had a bare bottom surface, the only fixation that the bone plate 162 would have when implanted would be provided by friction from the bone screws implanted in the bone. By attaching the fixation material 164 to the bottom surface of the bone plate 162, the bone plate 162 is provided with adhesive force of its own: initially from the roughness of the fixation material and later from bone ingrowth into the fixation material 164. Although the fixation material 164 is shown covering the entire bottom surface of the bone plate 162, the amount of fixation material 164 could be altered to provide a desired amount of adhesive force to the bone plate.

Figure 21:
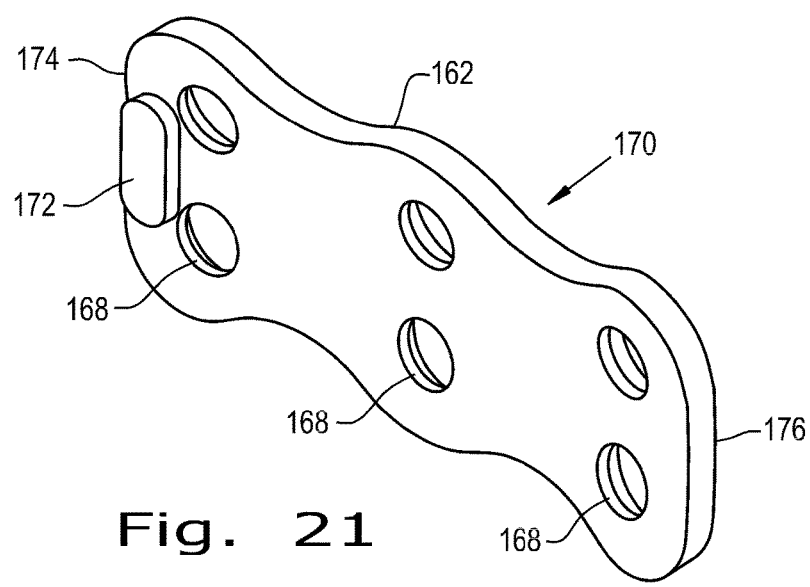
FIG. 21 is a perspective view of yet another embodiment of an orthopaedic implant of the present invention.

Referring now to FIG. 21, an orthopaedic implant 170 is shown that includes the bone plate 162 of FIGS. 19 and 20 with a fixation material 172 attached at one end 174 of the bone plate 162. The fixation material 172 is shaped as a patch and can be any fixation material previously described.

By attaching the fixation material 172 to only one end 174 of the bone plate 162, bone ingrowth and fixation will only occur at the end 174 of the plate with the fixation material 172, allowing an opposite end 176 to float to whatever degree the attached bone screws allow. Such a configuration allows for a dynamic bone plate 170.

Figure 22:
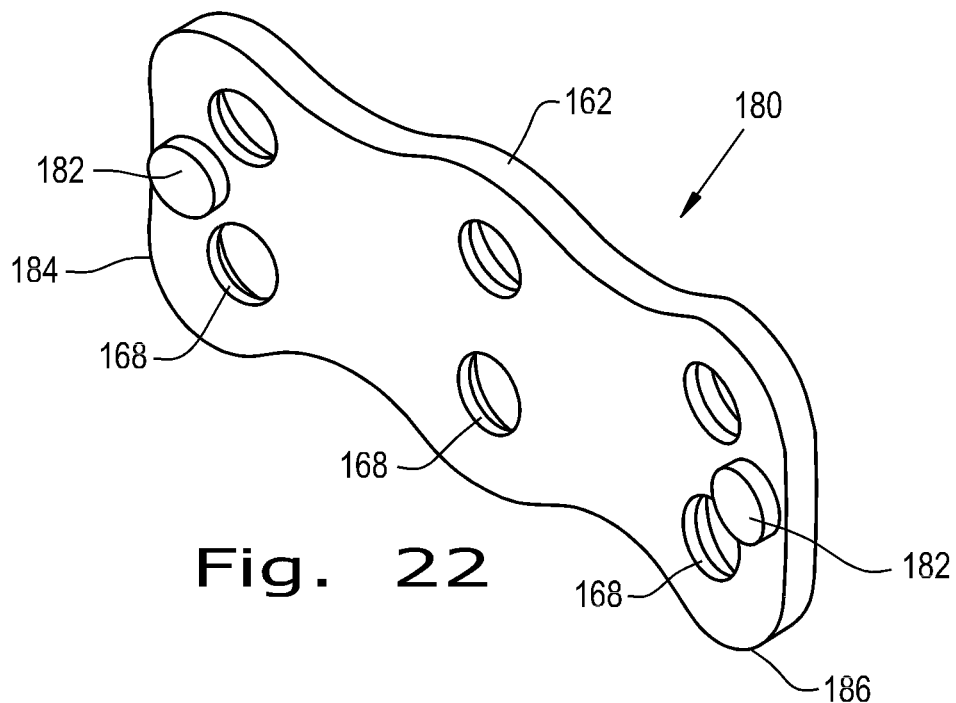
FIG. 22 is a perspective view of yet another embodiment of an orthopaedic implant of the present invention.

Referring now to FIG. 22, an orthopaedic implant 180 is shown that includes the bone plate 162 of FIGS. 19, 20 and 21 with two regions of a fixation material 182 attached at both ends 184, 186 of the bone plate 162. The regions of fixation material 182 are shaped as dots of material and can be any fixation material previously described. Attaching the fixation material 182 to both ends 184, 186 of the bone plate 162 provides bone ingrowth, and therefore fixation, at both ends 184, 186 of the bone plate 162.

Figure 23:
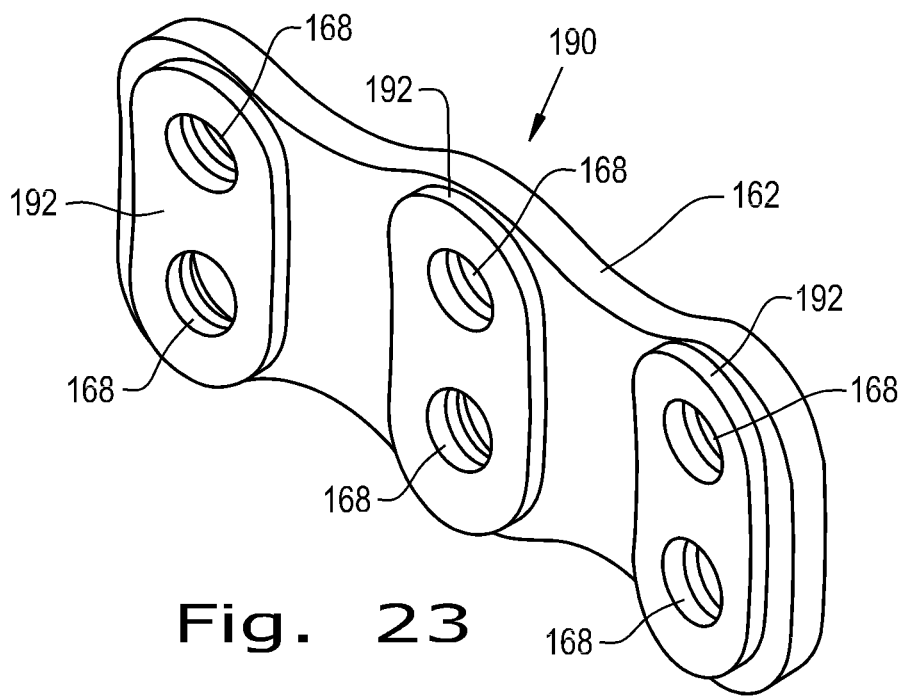
FIG. 23 is a perspective view of yet another embodiment of an orthopaedic implant of the present invention.

Referring now to FIG. 23, an orthopaedic implant 190 is shown that includes the bone plate 162 of FIGS. 19, 20, 21 and 22 with three regions of a fixation material 192 surrounding the openings 168 of the bone plate 162. The fixation material 192 can be any fixation material previously described. Bone ingrowth into the fixation material 192 around the openings 168 provide additional fixation to the bone plate 162 in those regions. Such a configuration could be desirable if the bone screws are to be removed after implantation or do not provide enough fixation of the bone plate 162 on their own.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of manufacturing an orthopaedic implant, comprising the steps of:
   providing a base device having a device surface;
   determining a minimally sufficient adhesive force to resist natural pull out caused by forces acting on said base device after implantation and bone ingrowth;
   determining a proper amount of a fixation material sufficient to provide an adhesive force equal to said minimally sufficient adhesive force;
   applying said fixation material to said device surface; and
   stopping application of said fixation material to said device surface when said proper amount of said fixation material is applied.

2. The method according to claim 1, further comprising the steps of:
   determining a proper placement of said proper amount of said fixation material to provide said adhesive force equal to said minimally sufficient adhesive force; and
   distributing said proper amount of said fixation material on said device surface in accordance with said proper placement.

3. The method according to claim 2, wherein said base device and said fixation material are composed of at least one of titanium, cobalt-chromium, and polyether ether ketone (PEEK).

4. The method according to claim 3, wherein said fixation material includes a roughened surface and a plurality of pores.

5. The method according to claim 2, wherein said proper placement is affected by at least one of a size of said base device, said device surface area, an intended implantation site, a diameter of said base device, and how proud said fixation material will be relative to said device surface.

6. The method according to claim 1, wherein applying said fixation material to said device surface comprises applying said fixation material to only a portion of said device surface.

7. The method according to claim 6, wherein said base device is a bone pin, and wherein applying said fixation material to said only said portion of said device surface comprises applying said fixation material as a band.

8. The method according to claim 7, wherein said bone pin has a diameter of approximately 0.05 inches, and said band has a width of approximately 0.02-0.125 inches and a thickness of approximately 0.005-0.015 inches.

9. The method according to claim 7, wherein said bone pin has a diameter of approximately 0.10 inches, and said band has a width of approximately 0.02-0.125 inches and a thickness of approximately 0.015-0.050 inches.

10. The method according to claim 6, wherein said base device is a bone screw including a head end, a distal end, and a plurality of threads formed on said device surface, and wherein applying said fixation material comprises applying said fixation material as either a patch or a dot to said only said portion of said device surface forming said distal end.

11. The method according to claim 6, wherein said base device is a bone screw including a head end, a distal end, and a plurality of threads formed on said device surface, and wherein applying said fixation material comprises applying said fixation material in a helical form to said only said portion of said device surface located between the plurality of threads.

12. The method according to claim 6, wherein said base device is a bone plate, and wherein applying said fixation material comprises applying said fixation material as a patch to said only said portion of said device surface located at a first end of said bone plate.

13. The method according to claim 6, wherein said base device is a bone plate, and wherein applying said fixation material comprises applying said fixation material as a first dot to said only said portion of said device surface located at a first end of said bone plate and as a second dot to said only said portion of said device surface located at a second end of said bone plate.

14. The method according to claim 6, wherein said base device is a bone plate including a plurality of openings, and wherein applying said fixation material comprises applying said fixation material as a region to said only said portion of said device surface surrounding each opening of said plurality of openings.

* * * * *